United States Patent [19]

Argyropoulos et al.

[11] Patent Number: 5,248,752

[45] Date of Patent: Sep. 28, 1993

[54] POLYURETHANE (METH)ACRYLATES AND PROCESSES FOR PREPARING SAME

[75] Inventors: John N. Argyropoulos, Scott Depot; Oliver W. Smith, Charleston; David R. Bassett, Charleston; Joseph V. Koleske, Charleston, all of W. Va.

[73] Assignee: Union Carbide Chemicals & Plastics Technology Corporation, Danbury, Conn.

[21] Appl. No.: 790,874

[22] Filed: Nov. 12, 1991

[51] Int. Cl.$^5$ .................................... C08G 18/28
[52] U.S. Cl. .................... 528/49; 560/158; 522/90; 526/301
[58] Field of Search ............ 560/158; 522/90; 526/301; 528/49

[56] References Cited

U.S. PATENT DOCUMENTS

| | | | |
|---|---|---|---|
| Re. 29,131 | 2/1977 | Smith et al. | 528/75 |
| 2,600,275 | 6/1952 | Smith | 568/494 |
| 2,624,764 | 1/1953 | Emerson et al. | 568/322 |
| 2,658,081 | 11/1953 | Emerson et al. | 568/678 |
| 2,680,118 | 6/1954 | Emerson et al. | 549/294 |
| 2,704,774 | 3/1955 | Gasson et al. | 568/483 |
| 2,809,186 | 10/1957 | Smith et al. | 568/853 |
| 2,829,169 | 4/1958 | Hagemeyer, Jr. et al. | 568/483 |
| 2,905,699 | 9/1959 | Kubler | 549/416 |
| 2,931,837 | 4/1960 | Stansbury, Jr. et al. | 568/679 |
| 2,964,571 | 12/1960 | Brannock | 568/858 |
| 3,046,311 | 7/1962 | Milligan | 568/862 |
| 3,282,946 | 11/1966 | Campbell et al. | 546/251 |
| 3,287,372 | 11/1966 | Brannock et al. | 549/416 |
| 3,299,074 | 1/1967 | Campbell | 546/251 |
| 3,912,785 | 10/1975 | Suzuki | 568/852 |
| 4,078,015 | 3/1978 | Leitheiser et al. | 525/440 |
| 4,094,914 | 6/1978 | Rottig et al. | 568/862 |
| 4,108,747 | 8/1978 | Crivello | 204/159.18 |
| 4,110,539 | 8/1978 | Albers et al. | 560/240 |
| 4,141,850 | 2/1979 | Readio et al. | 252/79.4 |
| 4,193,799 | 3/1980 | Crivello | 430/319 |
| 4,216,288 | 8/1980 | Crivello | 430/280 |
| 4,246,391 | 1/1981 | Watson, Jr. | 528/49 |
| 4,256,828 | 3/1981 | Smith | 430/280 |
| 4,394,525 | 7/1983 | Vogel et al. | 568/462 |
| 4,559,118 | 12/1985 | Heil et al. | 522/96 |
| 4,740,639 | 4/1988 | Beavers | 568/853 |
| 4,876,275 | 10/1989 | Himmele et al. | 514/452 |
| 5,043,221 | 8/1991 | Koleske | 428/413 |

OTHER PUBLICATIONS

Chemical Abstracts, vol. 79, 1973, 41899z, Apr. 1973.
Chemical Abstracts, vol. 92, 1980, 215204e.
Chemical Abstracts, vol. 88, 1978, 62910x.
Tautscher, C. J., Protective Circuit Coatings, Novatech Research Corporation, Redmond, WA, 1981.
Waryold, John, How to Select a Conformal Coating for Printed Circuit Boards, Insulation/Circuits, Jul. 1974.
ASTM D 16-84, Jul., 1984.

Primary Examiner—John Kight, III
Assistant Examiner—Rachel Johnson
Attorney, Agent, or Firm—G. L. Coon

[57] ABSTRACT

This invention relates to polyurethane (meth)acrylates that are prepared from certain liquid hydrocarbon diols and/or derivatives of said liquid hydrocarbon diols, polyfunctional isocyanates, and hydroxyalkyl acrylates and methacrylates. The polyurethane (meth)acrylates are useful as decorative and functional coatings, inks, adhesives, sealants, and formed parts.

26 Claims, No Drawings

POLYURETHANE (METH)ACRYLATES AND PROCESSES FOR PREPARING SAME

RELATED APPLICATIONS

The following are related, pending applications, filed on Nov. 12, 1991.

U.S. patent application Ser. No. 07/790873; U.S. patent application Ser. No. 07/790896; U.S. patent application Ser. No. 07/790895; and U.S. patent application Ser. No. 07/867,084 filed Apr. 14, 1992 and U.S. patent application Ser. No. 07/790872 now abandoned.

BRIEF SUMMARY OF THE INVENTION

1. Technical Field

This invention relates to polyurethane (meth)acrylates that are prepared from certain liquid hydrocarbon diols and/or derivatives of said liquid hydrocarbon diols, polyfunctional isocyanates, and hydroxyalkyl acrylates and methacrylates. The polyurethane (meth)acrylates are useful in a wide variety of decorative and functional coatings, inks, adhesives, and sealants that are usually formulated with other (meth)acrylates and with photoinitiators that generate free radicals when exposed to actinic energy. These polyurethane (meth)acrylates have excellent water-resistance characteristics.

2. Background of the Invention

Polyurethane (meth)acrylates are well known articles of commerce and various types of these compounds are marketed for coatings, inks, and sealant formulations that are cured with actinic energy. Polyurethane (meth)acrylates are compounds prepared by first end capping a polyol, $(HO)_q$—(POLYOL) with q usually 2 or 3, with diisocyanates, OCN—Z'—NCO, and then finally capping the remaining free isocyanates with a hydroxyalkyl compound such as hydroxyethyl acrylate, $CH_2=CHCOOCH_2CH_2OH$, and this may be described by the following idealized structural formula when a difunctional polyol is used and hydroxyethyl acrylate is the final capping compound:

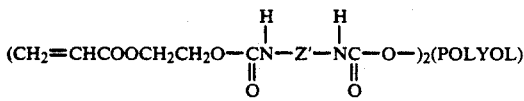

wherein Z' is a substituted or unsubstituted hydrocarbon residue described in the art and POLYOL is a substituted or unsubstituted hydrocarbon residue described in the art. Those skilled in the manufacture of such compounds are aware that the above is an idealized structure because molecular chain extension takes place when the polyol is first end capped with the diisocyanate and as a result a mixture of products with higher than expected molecular weight than that indicated by the idealized structure results.

However, even though polyurethane (meth)acrylates are commercial products, improvements such as lower viscosity and improved moisture resistance and permeability as compared to existing products are needed for various end uses, and polyurethane (meth)acrylates with either or both of these attributes would be desirable, useful compounds.

U.S. Pat. Reissue No. 29,131 describes unsaturated acrylate-capped polycaprolactone polyol derivatives that are produced from polycaprolactone polyols, organic isocyanates, and hydroxyethyl acrylate. These acrylate-capped products can be cured to form solid, protective films.

U.S. Pat. No. 4,078,015 describes ultraviolet light curable compositions that contain from 50 to 90 parts by weight of a polymerizable polyurethane product that is the reaction product of an organic diisocyanate, a beta-hydroxy alkyl ester of acrylic acid, and a polyol.

U.S. Pat. No. 4,246,391 describes a procedure for preparation of acrylated urethanes that have low viscosity. The procedure involves a process in which a monohydroxyl functional acrylate is first reacted with the polyisocyanate followed by reaction of this product mixture with a polyol.

DISCLOSURE OF THE INVENTION

It has been discovered that useful polyurethane (meth)acrylates can be prepared from certain liquid hydrocarbon diols such as 2-ethyl-3-propyl-1,5-pentanediol and/or derivatives of said liquid hydrocarbon diols, polyfunctional isocyanates such as toluene diisocyanate, hydroxyalkyl acrylates and methacrylates such as hydroxyethyl acrylate or methacrylate, and optionally other polyols. The liquid hydrocarbon diols are comprised of primary hydroxyl groups and 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less.

This invention also relates to a process for preparing polyurethane (meth)acrylates which comprises (i) contacting a liquid hydrocarbon diol comprised of primary hydroxyl groups and 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less, and/or a derivative of said liquid hydrocarbon diol, and optionally other polyols, with a polyfunctional isocyanate to form an isocyanate-capped prepolymer, and (ii) contacting said isocyanate-capped prepolymer with a hydroxyalkyl (meth)acrylate to form said polyurethane (meth)acrylate.

This invention further relates to a process for preparing polyurethane (meth)acrylates which comprises contacting a liquid hydrocarbon diol comprised of primary hydroxyl groups and 8 or more carbon atoms in which the primary hyroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less, and/or a derivative of said liquid hydrocarbon diol, and optionally other polyols, with a polyfunctional isocyanate and a hydroxyalkyl (meth)acrylate to form said polyurethane (meth)acrylate.

The polyurethane (meth)acrylates have a variety of uses as for example in formulations where it is compounded alone with a free radical-generating photoinitiator or in combination with other acrylates and methacrylates and a free radical generating photoinitiator. In addition, combinations of the above systems may be employed. The polyurethane (meth)acrylates are useful in both decorative and functional coatings, conformal coatings for printed circuit boards, inks, sealants, and adhesives and in shaped-part production such as that produced by stereolithography curable with actinic radiation, particularly with ultraviolet light, certain visible light of about 400 to 600 nm, and electron beams. Although the coatings have good adhesion to a variety of substrates, they can be formulated into particularly useful release coatings.

DETAILED DESCRIPTION

Polyurethane (meth)acrylates can be prepared from certain liquid hydrocarbon diols and/or derivatives of said liquid hydrocarbon diols, polyisocyanates, hydroxyalkyl (meth)acrylates and optionally other polyols and can be represented by the formula:

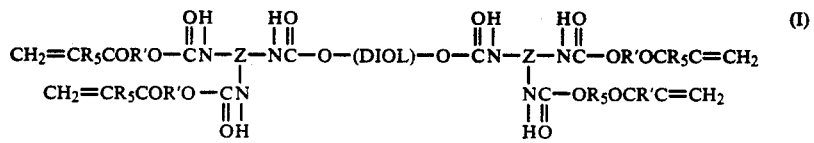

wherein $R_5$ is the same or different and is hydrogen or methyl, $R'$ is the same or different and is a linear or branched alkyl group of about 2 to 6 carbon atoms, preferably 2 or 3 carbon atoms, Z is the same or different and is a substituted or unsubstituted hydrocarbon residue, and DIOL is the hydrocarbon residue of a liquid hydrocarbon diol comprised of primary hydroxyl groups and 8 or more carbon atoms in which the primary hydroxy groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less.

The polyurethane (meth)acrylates can be prepared by first reacting a polyfunctional isocyanate, $Z—(NCO)_n$, preferably a diisocyanate, with HO—(DIOL)—OH to form an essentially isocyanate-capped prepolymer represented by the formula:

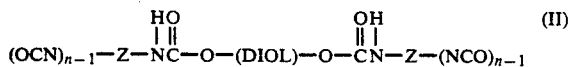

wherein Z and DIOL are as defined above and n has a value of 2 or 3, preferably 2. It is preferred that the isocyanate-capped prepolymer be prepared in an inert atmosphere such as a dry nitrogen or argon atmosphere. The isocyanate-capped prepolymer of Formula II is then reacted with a hydroxyalkyl (meth)acrylate, $CH_2=CR_5COR'OH$, to form the polyurethane (meth)acrylates of Formula I It is preferred that the polyurethane (meth)acrylates of the invention be prepared in an oxygen-containing atmosphere such as air to minimize or prevent polymerization of the acrylate functionality. Although optional, it is preferred that a stabilizer that prevents polymerization of acrylates, such as hydroquinone, be added to the reaction mass during the portion of the reaction in which hydroxyalkyl (meth)alkylate is reacting with the Formula II prepolymer. The stabilizer can be added before addition of the hydroxyalkyl (meth)acrylate, during its reaction with the Formula II prepolymer, or after completion of its reaction with the Formula II prepolymer, but it is preferred that it be added before addition of the Formula II prepolymer. It is understood by those skilled in art of isocyanate/ hydroxyl reactions that molecular chain extension can take place when the polyol is first end capped with the polyisocyanate and as a result a mixture of products with higher molecular weight and attendant viscosity than that expected from the idealized structure of Formula II results. Although the order of addition of the ingredients can be varied from the above description, it is thought that a minimum viscosity will result from the above described procedure.

The amount of liquid hydrocarbon diol and polyol to be used for preparation of the polyurethane (meth)acrylates of this invention is not narrowly critical; however, it is preferably equal to the number of equivalents of isocyanate minus one so that an essentially isocyanate-capped prepolymer as depicted in Formula II is obtained. The amount of hydroxyalkyl (meth)acrylate to be used for preparation of the polyurethane (meth)acrylates of this invention is not narrowly critical; however, it is preferably equal to the number of equivalents of isocyanate plus one so that an essentially (meth)acrylate-capped polyurethane as depicted in Formula I is obtained.

HO—(DIOL)—OH can preferably be represented by the formula:

wherein $R''$ is a substituted hydrocarbon residue having 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less.

Other preferred liquid hydrocarbon diols useful for preparation of the polyurethane (meth)acrylates of this invention are represented by the formula:

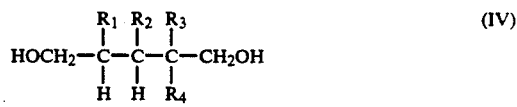

wherein $R_1$ is hydrogen or linear or branched alkyl having 1 to 3 carbon atoms, and $R_2$, $R_3$, and $R_4$ are the same or different and are hydrogen or linear or branched alkyl having 1 to 4 carbon atoms, said liquid hydrocarbon diol existing as a liquid at a temperature of 35° C. or less; provided (a) at least 2 of $R_1$, $R_2$, $R_3$, and $R_4$ are other than hydrogen; (b) the total number of carbon atoms in $R_1$, $R_2$, $R_3$, and $R_4$ together is 5 or more except as follows: (i) when $R_2$ is ethyl and one of $R_1$, $R_3$, and $R_4$ is methyl, then the remaining 2 of $R_1$, $R_3$, and $R_4$ can be hydrogen; (ii) when $R_3$ and $R_4$ are independently methyl and propyl, then $R_1$ and $R_2$ can be hydrogen; and (iii) when $R_1$ is methyl and $R_2$ is ethyl and one of $R_3$ and $R_4$ is methyl, then the remaining $R_3$ or $R_4$ can be hydrogen; (c) when the total number of carbon atoms in $R_1$ and $R_2$ is 4 or more, then the total number of carbon atoms in $R_2$ is 3 or less except when $R_1$ is propyl and $R_3$ and $R_4$ are hydrogen, then $R_2$ can be butyl; and (d) when $R_1$ is ethyl and $R_2$ is propyl, then $R_3$ is other than ethyl. It is preferred that one of $R_3$ or $R_4$ be hydrogen and that the total number of carbon atoms contained in $R_1$ to $R_4$ is 3 to 7, and it is most preferred that $R_3$ and $R_4$ be hydrogen and $R_1$ and $R_2$ contain a total of 4 to 6 carbon atoms. For example, if $R_1$ is $CH_3CH_2-$, $R_2$ is $CH_3CH_2CH_2-$, and $R_3$ and $R_4$ are hydrogen, there would be a total of 5 carbon atoms contained in $R_1$ to $R_4$; and if $R_1$ is ethyl, $R_2$ is butyl, $R_3$ is propyl, and $R_4$ is ethyl, there would be a total of 11 carbon atoms contained in $R_1$ to $R_4$.

The liquid hydrocarbon diols useful in this invention, for example, the liquid 1,5-pentanediols represented by Formula IV above, can be prepared by a process comprising:

(a) contacting a substituted vinyl ether with a substituted or unsubstituted acrolein to form a substituted 3,4-dihydropyran;

(b) contacting the substituted 3,4-dihydropyran with an acid catalyst to form a substituted dialdehyde; and (c) hydrogenating the substituted dialdehyde in the presence of a catalyst to form a liquid hydrocarbon diol represented by Formula IV above.

More, particularly, the liquid 1,5-pentanediols represented by Formula IV above can be prepared by reacting acrolein or substituted acrolein with a substituted vinyl ether as follows:

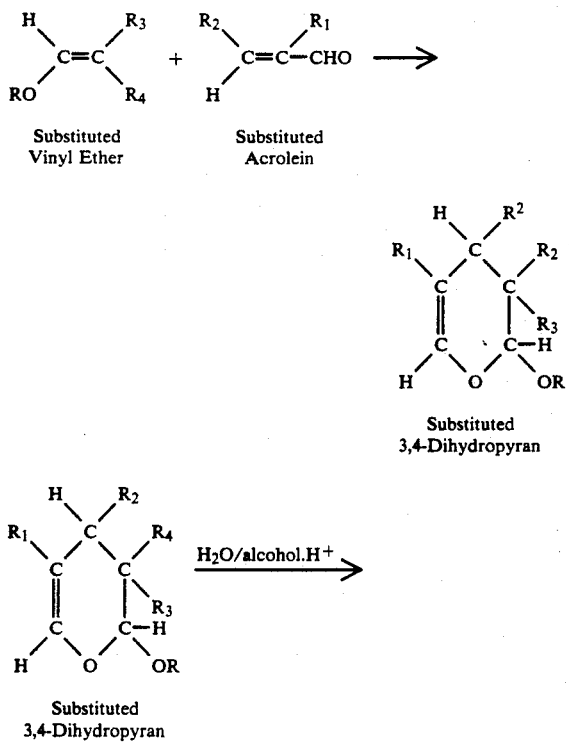

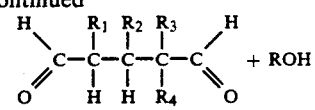

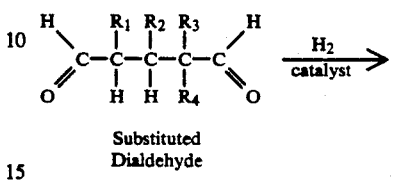

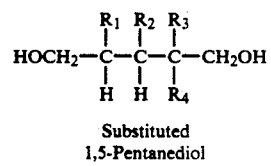

wherein $R_1$, $R_2$, $R_3$ and $R_4$ are as defined above and R is a substituted or unsubstituted hydrocarbon residue, preferably a linear or branched alkyl having from 1 to about 8 carbon atoms.

Illustrative of suitable substituted vinyl ethers useful in preparing the liquid hydrocarbon diols include, among others, alkyl vinyl ethers such as methyl vinyl ether; methyl (2-methyl vinyl) ether which has the structure:

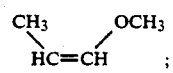

methyl (2-ethyl vinyl) ether, which has the structure:

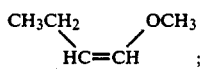

methyl (2,2-dimethyl vinyl) ether; methyl (2-methyl, 2-propyl vinyl) ether; methyl (2-butyl, 2-methyl vinyl) ether; ethyl vinyl ether; ethyl (2-methyl vinyl); ethyl (2-ethyl vinyl) ether; ethyl (2,2-dimethyl vinyl) ether; ethyl (2-methyl, 2-propyl vinyl) ether; ethyl (2-butyl, 2-methyl vinyl) ether; n-propyl and i-propyl vinyl ethers; butyl vinyl ethers such as n-butyl vinyl ether, s-butyl vinyl ether, i-butyl vinyl ether, and t-butyl vinyl ether; amyl vinyl ethers, and the like; divinyl ethers such as triethylene glycol divinyl ether, 1,4-cyclohexane dimethanol divinyl ether, trivinyl ethers, and the like. It is preferred that alkyl vinyl ethers with up to 3 carbon alkyl groups and one- to three-carbon alkyl (alkyl vinyl) ethers with alkyl vinyl groups of up to 8 carbon atoms are used.

Illustrative of suitable acroleins useful in preparing the liquid hydrocarbon diols include, among others, acrolein; 2-ethyl-2-butenal; 2-methyl-2-butenal; 2-(n-propyl)-2-butenal; 2-(i-propyl)-2-butenal; 2-methyl-2-pentenal, which has the structure:

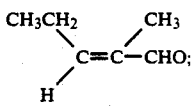

2-(i-propyl)-2-pentenal; 2-(n-butyl)-pentenal; 2-(i-butyl)-pentenal; 2-(s-butyl)-pentenal; 2-(t-butyl)-pentenal; 2-amyl pentenals; 2-ethyl-2-hexenal, which has the structure:

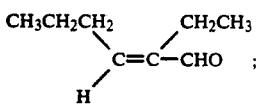

2-methyl-2-hexenals; 2-(n-propyl)-2-hexenals; 2-(i-propyl)-2-hexenals; 2-(n-butyl)-2-hexenals; 2-(i-butyl)-2-hexenals; 2-(s-butyl)-2-hexenals; 2-(t-butyl)-2-hexenals; 2-amyl hexenals; and the like.

Illustrative of suitable substituted 3,4-dihydropyrans prepared in reaction step (a) above include, for example, 2-alkoxy-5-ethyl-4-propyl-3,4-dihydro-1,2-pyran, 2-alkoxy-4-ethyl-5-methyl-3,4-dihydro-1,2-pyran, 2-alkoxy-4-ethyl-3,5-dimethyl-3,4-dihydro-1,2-pyran, 2-alkoxy-5-ethyl-3-methyl-4-propyl-3,4-dihydro-1,2-pyran, 2-alkoxy-3,4-diethyl-5-methyl-3,4-dihydro-1,2-pyran, 2-alkoxy-4-ethyl-3,3',5-trimethyl-3,4-dihydro-1,2-pyran, 2-alkoxy-3,3'-dimethyl-4-propyl-3,4-dihydro-1,2-pyran, 2-alkoxy-3-methyl-3'-propyl-3,4-dihydro-1,2-pyran, 2-alkoxy-4-ethyl-5-methyl-3-methyl-3'-propyl-3,4-dihydro-1,2-pyran, 2-alkoxy-5-ethyl-3-methyl-3',4-dipropyl-3,4-dihydro-1,2-pyran, 2-alkoxy-3-butyl-3'-ethyl-3,4-dihydro-1,2-pyran, 2-alkoxy-3-butyl-3',4-diethyl-5-methyl-3,4-dihydro-1,2-pyran, 2-alkoxy-3-butyl-3',5-diethyl-4-propyl-3,4-dihydro-1,2-pyran, and the like. For purposes of these illustrative substituted 3,4-dihydropyrans, alkoxy refers to methoxy, ethoxy, n-propoxy, isopropoxy, n-butoxy, i-butoxy, s-butoxy, t-butoxy, and the like.

The step (a) reaction can be conducted at a temperature of from about 160° C. to 280° C. for a period of about 1 hour to about 7 days with the longer time being used at the lower temperature, preferably from about 180° C. to about 270° C. for about 1 hour to about 5 days, and more preferably at about 200° C. to 260° C. for about 1 hour to about 48 hours. During the reaction, from less than 0.01 percent by weight to about 5 percent by weight of the total weight of the starting materials, preferably from about 0.01 percent by weight to about 2 percent by weight, of a free radical inhibitor can be added to the reaction mass. Illustrative of such free radical inhibitors are 2,6-ditertiarybutyl-4-methyl phenol, hydroquinone, hydroquinone monomethyl ether, and the like. A particularly useful inhibitor is hydroquinone.

The step (a) reaction can be conducted over a wide range of pressures ranging from atmospheric pressure to superatmospheric pressures, e.g., from about 1 atmosphere to about 100 atmospheres or greater. It is preferable to conduct the step (a) reaction at pressures of from about atmospheric to about 75 atmospheres. The step (a) reaction is preferably effected in the liquid or vapor states or mixtures thereof.

The molar ratio of substituted vinyl ether to acrolein compound in the step (a) reaction is not narrowly critical and can range from about 0.05:1 or less to about 50:1 or greater, preferably from about 0.1:1 to about 10:1.

Illustrative of acid catalysts suitable for ring opening of the substituted 3,4-dihydropyran intermediates to form substituted dialdehydes in accordance with reaction step (b) above are mineral acids, including sulfuric acid, hydrochloric acid, phosphoric acid, triflic acid and its salts, sulfonic acids; organic acids including acetic acid, chloroacetic acid, oxalic acid; crosslinked acidic resins such as the various ion exchange resins including Amberlite® CG-400, Amberlite® IR-118; Amberlite® IR120(plus), Dowex® MSC-1, Dowex® M-31, Dowex® M32, Dowex® 50X2-100, Dowex® 50X2-200, Dowex® 50X2-400, Dowex® 50X4-400, Dowex® 50X8-100, Dowex® 50X8-200, Dowex® 50X8-400, Nafion® 117, Nafion® 417, Nafion® NR50, Nafion® perfluorinated powder, similar crosslinked acidic resins; perfluorinated polymers which contain sulfonic acid groups such as XUS-40036.02 (Dow Chemical Company); and the like. The illustrative ion exchange resins above, as well as others, are available from Aldrich Chemical Company, Inc.

The acid catalysts employed in the ring-opening of the substituted 3,4-dihydropyran intermediates are preferably used in conjunction with water; alcohols such as methanol, ethanol, isopropanol, n-propanol, n-butanol, sec-butanol, isobutanol, and tert-butanol, amyl alcohols as well as higher alcohols; glycol ethers such as ethoxy ethanol, methoxy ethanol, 1-methoxypropane, methoxyethoxy ethanol; glyme; and the like, as well as mixtures of water and other solvents. The amount of acid catalyst used in reaction step (b) is dependent on the particular catalyst employed and can range from about 0.01 weight percent or less to about 10 weight percent or greater of the total weight of the starting materials.

The acid dialdehyde reaction mass can be washed with water and/or aqueous solution of neutralizing agents. Illustrative of such neutralizing agents are sodium acetate, potassium acetate, sodium bicarbonate, sodium carbonate, potassium bicarbonate, potassium carbonate, and the like.

Illustrative of suitable substituted dialdehydes prepared in reaction step (b) above include, for example, 3-ethyl-2-methyl-1,5-pentanedial, 2-ethyl-3-propyl-1,5-pentanedial, 3-ethyl-2,4-dimethyl-1,5-pentanedial, 2-ethyl-4-methyl-3-propyl-1,5-pentanedial, 3,4-diethyl-2-methyl-1,5-pentanedial, 3-ethyl-2,4,4'-trimethyl-1,5-pentanedial, 2-ethyl-4,4'-dimethyl-3-propyl-1,5-pentanedial, 2-methyl-2'-propyl-1,5-pentanedial, 3-ethyl-2,4-dimethyl-4'-propyl-1,5-pentanedial, 2-ethyl-4-methyl-3,4'-dipropyl-1,5-pentanedial, 2-butyl-2'-ethyl-1,5-pentanedial, 4-butyl-3,4-diethyl-2-methyl-1,5-pentanedial, 4-butyl-2,4'-diethyl-3-propyl-1,5-pentanedial, and the like.

The step (b) reaction can be conducted over a wide range of pressures ranging from atmospheric or subatmospheric pressures to superatmospheric pressures, e.g., from about 1 atmosphere or less to about 25 atmospheres or greater. It is preferable to conduct the step (b) reaction at pressures of from about 1 atmosphere to about 10 atmospheres. The step (b) reaction is preferably effected in the liquid or vapor states or mixtures thereof.

The temperature of the step (b) reaction may be as low as about ambient temperature to about 300° C. Preferably, the reaction temperature ranges from about 50° C. to about 200° C., and more preferably from about 60° C. to about 120° C.

Illustrative of catalysts useful in the hydrogenation step (c) involving reduction of substituted dialdehydes include, for example, Raney-type compounds such as Raney nickel and modified Raney nickels; molybdenum-promoted nickel, chromium-promoted nickel, cobalt-promoted nickel; platinum; palladium; iron; cobalt molybdate on alumina; copper chromite; barium promoted copper chromite; tin-copper couple; zinc-copper couple; aluminum-cobalt; aluminum-copper; and aluminum-nickel; platinum; nickel; and the like. The amount of hydrogenation catalyst used in step (c) is dependent on the particular catalyst employed and can range from about 0.01 weight percent or less to about 10 weight percent or greater of the total weight of the starting materials.

The particular reaction conditions for the step (c) hydrogenation reaction are not narrowly critical, and can be any effective hydrogenation procedures sufficient to produce the substituted 1,5-pentanediols of this invention. The step (c) reaction can be carried out at temperatures of from about ambient temperature to about 250° C., preferably from about 70° C. to about 200° C., and more preferably from 90° C. to 150° C. The step (c) reaction preferably may be conducted at pressures of from about 5 atmospheres to about 100 atmospheres, and more preferably from about 10 atmospheres to about 75 atmospheres.

Illustrative of suitable substituted 1,5-pentanediols useful in preparing the polyurethane (meth)acrylates of this invention include, for example, 3-ethyl-2-methyl-1,5-pentanediol, 2-ethyl-3-propyl-1,5-pentanediol, 2,4-dimethyl-3-ethyl-1,5-pentanediol, 2-ethyl-4-methyl-3-propyl-1,5-pentanediol, 2,3-diethyl-4-methyl-1,5-pentanediol, 3-ethyl-2,2,4-trimethyl-1,5-pentanediol, 2,2-dimethyl-4-ethyl-3-propyl-1,5-pentanediol, 2-methyl-2-propyl-1,5-pentanediol, 2,4-dimethyl-3-ethyl-2-propyl-1,5-pentanediol, 2,3-dipropyl-4-ethyl-2-methyl-1,5-pentanediol, 2-butyl-2-ethyl-1,5-pentanediol, 2-butyl-2,3-diethyl-4-methyl-1,5-pentanediol, 2-butyl-2,4-diethyl-3-propyl-1,5-pentanediol, 3-butyl-2-propyl-1,5-pentanediol and the like, including mixtures thereof.

Illustrative derivatives based on the liquid hydrocarbon diols that are useful in preparing the polyurethane (meth)acrylates of this invention include, for example, polyesters, silicone-containing compounds, polyols initiated with said diols, and the like, including mixtures thereof. This invention is not intended to be limited in any manner by the permissible derivatives of liquid hydrocarbon diols.

The polyester derivative products useful in this invention include, for example, those represented by the structural formula:

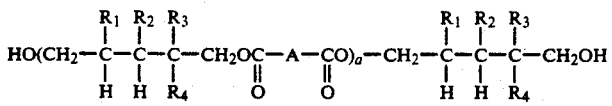

wherein $R_1$ is the same or different and is hydrogen or linear or branched alkyl having from 1 to 3 carbon atoms, $R_2$, $R_3$ and $R_4$ are the same or different and are hydrogen or linear or branched alkyl having from 1 to 4 carbon atoms, A is the same or different and is a substituted or unsubstituted hydrocarbon residue, preferably aryl such as phenylene, substituted phenylene, alkyl, cyclohexyl, substituted cyclohexyl and the like, and a is a value from about 1 to about 300 or greater, preferably from 1 to about 150, and more preferably from about 1 to about 75 or less.

Optionally, up to about 60 weight percent, preferably up to about 40 weight percent of other di-, tri-, tetra-, and higher-functionality polyols may be used in combination with the liquid hydrocarbon diols of Formula IV to form the polyesters of Formula V. Suitable polyols include, for example, ethylene glycol, diethylene glycol, propylene glycol, dipropylene glycol, polyoxypropylene diols and triols, neopentyl glycol, esterdiols such as Esterdiol-204 and ethoxylated and propoxylated esterdiols, ethylene oxide/propylene oxide copolymer polyols, polyether polyols, polycarbonate polyols, poly(alkylene oxide) polyols, 1,3-propanediol, 1,4-butanediols, poly(tetramethylene oxide) polyols, 1,5-pentanediols other than those of Formula IV, 1,6-hexanediols, 2-ethyl-1,3-hexanediol, 1,7-heptanediol, and higher linear and branched hydrocarbon diols, polylactone diols and triols such as the poly-c-caprolactone polyols; halogenated diols such as 3-chloro-1,2-propanediol, 2,3-dibromo-1,4-butanediol; triols and higher hydroxyl-functional polyols such as trimethylolpropane, pentaerythritol, dipentaerythritol, sorbitol, sucrose; hydroquinone and substituted hydoquinones, bisphenols such as Bisphenol A, Bisphenol C, Bisphenol F, as well as others; 1,2-cyclohexanediols, 1,3-cyclohexanediols, 1,4-cyclohexanediols, 1,4-cyclohexane dimethanol, xylenediols, 2,2,4,4-tetramethyl-1,3-cyclobutanediol, and the like, including mixtures thereof.

Illustrative of the polyfunctional carboxylic acids that can be used to prepare the polyester derivative products useful in this invention include, for example, oxalic acid, malonic acid, succinic acid, glutaric acid, adipic acid, pimelic acid, suberic acid, azelaic acid, sebacic acid, undecanedioic acid, dodecanedioic acid, tridecanedioic acid, maleic acid, fumaric acid, 2-methyl-cis-2-butenedioic acid, 2-methylenesuccinic acid, 1,1-cyclobutanedicarboxylic acid, norcamphoric acid, tetrahydrophthalic acid, methyl-tetrahydrophthalic acid, 1,1-cyclohexanedicarboxylic acid, hexahydrophthalic acid, 1,4-cyclohexanedicarboxylic acid, chlorendic acid, 1,4-benzenediacetic acid, phthalic acid, isophthalic acid, trimellitic acid, any other polyfunctional carboxylic acid including those having substituents thereon such as alkyl or alkoxy groups, nitro, halogen, aryl, carboxyl or any other group that will not unduly interfere with the reaction and the like as well as mixtures of such acids and mixtures of such acids with acid anhydrides.

Illustrative of the acid anhydrides that can be used to prepare the polyester derivative products useful in this invention include, for example, trimellitic anhydride, tetrahydrophthalic anhydride, phthalic anhydride, isophthalic anhydride, benzophenone dicarboxylic acid anhydride, succinic anhydride, glutaric anhydride, napthoic anhydride, clorendic anhydride, itaconic anhydride, maleic anhydride, or any other intramolecular anhydride including those having substituents thereon such as alkyl or alkoxy groups, nitro, halogen, aryl, carboxyl or any other group that will not unduly interfere with the reaction and the like as well as mixtures of anhydrides or mixtures of anhydrides and polyfunctional carboxylic acids.

The polyester derivatives can be prepared by heating conventional amounts of the liquid hydrocarbon diols, optional polyols, polyfunctional carboxylic acids and/or acid anhydrides at an elevated temperature and removing water of condensation. The process of condensation is rate enhanced if catalysts are used. The catalysts that may be used to prepare the polyesters useful in the compositions of this invention are those known to persons skilled in the art of polyester preparation, illustrative of which are dibutyltin oxide, antimony oxide, tin oxide, titanium alkoxides, alkali metal salts or metallic salts of manganese, cadmium, magnesium, zinc, cobalt, tin, and the like.

The silicone-containing derivative compounds useful in the coating compositions of the invention can be prepared by conventional methods by either end capping, coupling, or other reaction when Formula IV liquid hydrocarbon diols or mixtures of Formula IV liquid hydrocarbon diols and optionally other polyols are reacted with silanes. Illustrative of the silane-containing derivative compounds include, for example, the following:

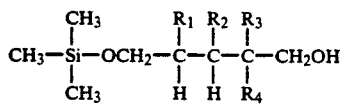

when 1 mole of trimethylchlorosilane and 1 mole of Formula IV diol are reacted,

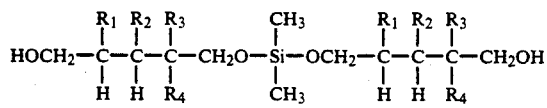

when one mole of dimethyldichlorosilane and two moles of Formula IV diol are reacted,

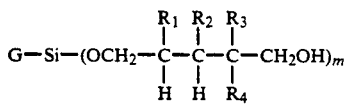

wherein $R_1$, $R_2$, $R_3$ and $R_4$ are as defined above, m is 3 or 4 and G is methyl when m is 3 and nonexistent when m is 4 when 3 moles (m=3) or 4 moles (m=4) of Formula IV diol are reacted with methyltrichlorosilane or tetrachlorosilane respectively, and the like. It is preferred that the silane-containing product have residual hydroxyl groups. It is understood by those skilled in the art that when polyfunctional compounds are combined, a variety of products, including chain extended products, can be obtained. Illustrative of the silanes that can be used to produce the silane-containing compounds useful in the compositions of the invention include, for example, chloroalkylchloro and arylchlorosilanes, diphenylethylchlorosilane, trimethylchlorosilane, dimethyldichloromethylsilane, triphenylchlorosilane, methyldichlorosilane, dimethylethylchlorosilane, dichlorosilane; alkoxysilanes such as methoxysilane, dimethoxysilane, diethyoxysilane, triethoxysilane, dimethylmethoxychlorsilane, dimethylmethoxysilane, tris(methoxy)-3-chloropropylsilane, and the like, including mixtures thereof.

Illustrative polyols that can be used in combination with the Formula IV liquid hydrocarbon diols in preparation of the silicone-containing derivative products useful in this invention include, for example, diethylene glycol, 1,4-butanediol, 1,6-hexanediol, 1,4-dihydroxyquinone, 2,2-dimethyl-1,3-propanediol, hydroxyl-terminated polyesters, ethylene oxide/propylene oxide copolymer polyols, poly(ethylene oxide) polyols, poly(alkylene oxide) polyols, polyether polyols, poly(tetramethylene oxide) polyols, polycarbonate polyols, polylactone polyols, and the like, including mixtures thereof.

The polyol derivative products formed by ring-opening polymerization and initiated with the liquid hydrocarbon diols of Formula IV and useful in this invention include, for example, polyols formed by reaction of one mole of the Formula IV compound and from about one to about 10 moles of $\epsilon$-caprolactone, substituted $\epsilon$-caprolactones, $\delta$-valerolactone, substituted $\delta$-valerolactones, or a mixture of such lactones or other copolymerizable lactones; or from 1 to about 10 moles of propylene oxide, epichlorohydrin, 1,2-butylene oxide, or ethylene oxide or mixtures of such oxides, with it preferred that from 1 to about 4 moles of ethylene oxide by used alone or in the mixtures. If desired both alkylene oxide and lactone units can be present in the polyols. Methods of preparation of such polyols are well known to those skilled in the art of lactone or alkylene oxide polymerization.

In an embodiment of this invention, 100 parts of HO—(DIOL)—OH can be blended with from about 1 to about 90 parts of other polyols before reaction with the polyfunctional isocyanate and hydroxyalkyl (meth)acrylate to form compositions that can have improved water resistance over those that would be obtained from polyurethane (meth)acrylates made from the other polyols alone.

The polyols that can be blended with HO—(DIOL)—OH are preferably dihydroxyl functional compounds, although up to about 15 percent by weight of trifunctional polyols can be used or up to about 5 weight percent of polyols with a hydroxyl functionality of greater than 3 can be used. Illustrative of the difunctional polyols useful for blending with HO—(DIOL)—OH to form the polyurethane (meth)acrylates of this invention include, for example, ethylene glycol, diethylene glycol, 1,4-butanediol, 1,6-hexanediol, 2,2,4-trimethyl-1,5-pentanediol, Esterdiol 204, ethoxylated and propoxylated Esterdiol 204, 1,4-cyclohexane dimethanol, 1,4-phenylene dimethanol; the various difunctional acrylateone polyols such as TONE®-0200, -0210, -0230, -0240, -0260, which are commercially available from Union Carbide Chemicals and Plastics Company Inc.; propylene glycol and dihydroxyl-functional poly(propylene oxide) polyols, poly(tetramethylene oxide) polyols, polyester polyols, polyether polyols, poly(alkylene oxide) polyols, polyoxyethylene polyols, polycarbonate polyols, and the like, including mixtures thereof. Illustrative of the trihydroxyl-functional and higher functional polyols are glycerol, trimethylolpropane, ethoxylated and propoxylated trimethylolpropane, trifunctional caprolactone polyols such as TONE®-0301, -0305, and 0-310, which are commercially available from Union Carbide Chemicals and Plastics Company Inc.; trihydroxyl-functional poly(propylene oxide) polyols including ethylene oxide-capred poly(propylene oxide) polyols, pentaerythritol, sorbitol, and the like, including mixtures thereof.

Illustrative of polyfunctional isocyanates that can be used to prepare the polyurethane (meth)acrylates of this invention include, for example, 2,4-toluene diisocyanate and 2,6-toluene diisocyanate as well as mixtures of these diisocyanates; 4,4'-diphenylmethane diisocyanate (MDI), 4,4'-dicyclohexyldiisocyanate or reduced MDI, meta- and para-tetramethyl xylene diisocyanate, 3-isocyanatomethyl-3,5,5-trimethylcyclohexylisocyanate or isophorone diisocyanate, hexamethylene diisocyanate, 1,5-naphthylene diisocyanate, dianisidine diisocyanate, di(2-isocyanatoethyl)bicyclo[2.2.1]-hept-5-ene-2,3-dicarboxylate, 2,2,4- and 2,4,4-trimethylenehexamethylene diisocyanate, 4,4',4"-triisocyanatotriphenylmethane, 4,4',4"-triisocyanate triphenylmethane, 2,4,6-triisocyanate toluene, and the like, including mixtures thereof. It is preferred that diisocyanates be used, but up to about 10 percent of the diisocyanate used can have isocyanate functionality greater than 2.

If desired, catalysts for the hydroxyl/isocyanate reactions to form urethane linkages may be used. Illustrative of such catalysts are the known urethane catalysts which can be used in conventional amounts and include the amines or organometallic compounds such as triethylamine, ethylene diamine tetraamine, morpholine, N-ethyl-morpholine, triethanolamine, piperazine, N,N,N',N'-tetramethyl- butane-1,3- diamine, dibutyltin dilaurate, dibutyltin oxide, stannous octanoate, stannous laurate, isoctyltin diacetate, lead octanoate, zinc octanoate, and the like.

It is preferred but not necessary that the reactions be carried out in an inert solvent such as toluene, benzene, xylene, and other aromatic hydrocarbons, heptane, octane, nonane, and other aliphatic hydrocarbons, methyl ethyl ketone, methyl i-butyl ketone, methyl amyl ketone, 2-ethoxyethyl acetate, 2-ethyoxybutyl acetate, and the like. Mixtures of such inert solvents may also be employed.

Reaction temperatures can vary from about 15° C. to about 100° C. or higher, preferably from about 40° C. to about 75° C., and most preferably from 40° C. to 60° C. The reaction time will vary according to the size of the batch of product being produced, the nature of the isocyanate employed, the nature of the hydroxyalkyl (meth)acrylate used, and the reaction temperature. It is preferred that the isocyanate/ HO—(DIOL)—OH reaction be carried out in a dry nitrogen atmosphere and the Formula II prepolymer/hydroxyalkyl (meth)acrylate reaction be carried out in an oxygen-containing atmosphere such as air and that a stabilizer be used in the latter step. If all three ingredients are reacted at the same time, it is preferred that a dry air or other oxygen-containing atmosphere be used.

Illustrative of hydroxyalkyl (meth)acrylates that can be used to prepare the polyurethane (meth)acrylates of this invention include, for example, hydroxyethyl acrylate, hydroxyethyl methacrylate, hydroxypropyl acrylate, hydroxypropyl methacrylate, and the like, including mixtures thereof. A preferred hydroxyalkyl (meth)acrylate is hydroxyethyl acrylate.

Illustrative of the stabilizers or free-radical inhibitors that can be used alone or in combination to prevent polymerization of acrylate functionality during the reaction of hydroxyalkyl acrylates with Formula II prepolymers are hydroquinone, 4-methoxyphenol, hydroquinone monomethyl ether, phenothiazine, benzoquinone, methylene blue, 2,5-di-t-butylhydroquinone, and other free radical inhibitors known in the art. Usually the inhibitors are used at a concentration of about 50 parts per million to about 1000 parts per million.

In an embodiment of this invention, acrylate-terminated compositions of the liquid hydrocarbon diols can be prepared by a condensation reaction in which acrylic acid or methacrylic acid or a mixture thereof is condensed with HO—R"—OH and optionally other polyols. An illustrative reaction scheme is as follows:

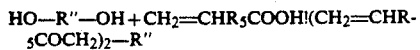

wherein R" and $R_5$ are as defined above. Such diacrylates are useful as reactive diluents in radiation-curable coating, ink, sealant, or adhesive compositions that are cured by electron beam or photochemical means.

Coating compositions containing the acrylate-terminated products of this invention can be cured by thermal or actinic energy or a combination of these energy sources. Particularly useful actinic energy sources are electron beams and ultraviolet light though certain portions of the visible light spectrum can be used when specific photoinitiators are employed. The coating compositions can contain from about 10 percent by weight to 100 percent by weight of the acrylate-terminated products of this invention exclusive of photoinitiators, catalysts, inert solvents, surfactants, flow and leveling agents, slip agents, thickeners, pigments, fillers, and other additives that are known to those skilled in the art of formulating coatings which can be used in conventional amounts. The remainder of from zero to about 90 percent by weight of the coating composition can include ethylenically unsaturated compounds, particularly acrylates and including commercially available, formulated acrylate products, and N-vinyl pyrrolidone.

Illustrative of the ethylenically unsaturated monomers include the esters of acrylic and methacrylic acid with monohydric and polyhydric compounds, such as methyl, ethyl, propyl, butyl, pentyl, hexyl, octyl, decyl, and the like acrylates and methacrylates as well as the various isomers of these and other listed compounds, neopentyl diacrylate, Esterdiol diacrylates such as 2,2-dimethyl-3-hydroxypropyl-2,2-dimethyl-3-hydroxypropionate diacrylate, trimethylolpropane triacrylate, pentaerythriol di-, tri-, and tetraacrylate, hyroxyethyl acrylate, hydroxypropyl acrylate, caprolactone acrylates, ethoxylated acrylates, propyoxylated acrylates, glycerol acrylates, triethylene glycol diacrylate, tetraethylene glycol diacrylate, ethoxyethyl acrylate, cyclohexyl acrylate, 2-phenoxyethyl acrylate, isobornyl acrylate, 1,3-butylene glycol diacrylate, 1,4-butanediol diacrylate, 1,6-hexanediol diacrylate, glycidyl acrylate, as well as the methacrylates of such compounds, and the like; styrene, divinylbenzene; N-vinylpyrrolidone, and the like. Illustrative of the oligomers or polymers which can be used in the photopolymerizable reaction formulations are poly(ethylene glycol) acrylates, caprolactone di-, tri-, and tetraacrylates, tripropylene glycol diacrylate, poly(propylene glycol) acrylates, ethoxylated or propoxylated Bisphenol A diacrylates, alkoxylated Esterdiol diacrylates such as ethoxylated or propoxylated 2,2-dimethyl-3-hydroxypropyl-2,2-dimethyl-3-hydroxypropionate diacrylates, acrylates of caprolactone reacted with Esterdiols, ethoxylated or propoxylated trimethylolpropane triacrylate, ethoxylated or propoxylated pentaerythriol di-, tri, or tetracrylate, unsaturated polyesters containing ethylenically unsaturated from maleic, fumaric, citraconic, and the like unsaturated dicarboxylic acids, urethane acrylates of various types, epoxy acrylates, acrylated polybutadiene, acrylated linseed oil, acrylated soybean oil, and the like. Compounds such as those mentioned are known to those skilled in the art and many are commercially available.

Illustrative of the formulated acrylate products to which the acrylate-terminated products of this invention can be added are Loctite 361 Activator/Resin combinations, Three Bond of America, Inc. under the designation 30A-040, and the like.

The acrylate-terminated compositions of this invention and the ethylenically unsaturated monomers, oligomers, and polymers employed in the photopolymerizable systems are combined with free radical photoinitiators when curing is to be accomplished by exposure to ultraviolet light. Illustrative of the photoinitiators are 2,2-diethoxyacetophenone, benzil, diacetyl, benzil and alkyl benzils, dimethoxyphenylacetophenone, benzoin ethers, alpha-alkyl benzoins, phenyl benzoin, 2,3-pentanedione, 2,3-octanedione, 2,2-dimethyl-4-3,4-butanedione, benzophenone, substituted benzophenones, and the like. It is understood by those skilled in the art that when benzophenone and similar compounds are used as photoinitiators, a synergistic agent, such as a tertiary amine or polymeric amine such as a secondary or primary amine terminated poly(propylene oxide) polyol are employed to enhance the conversion of photoadsorbed energy to polymerization-initiating free radicals. The coating compositions generally contain from 0.01 to about 10 weight percent based on the weight of the coating composition, preferably from about 0.1 to about 6 weight percent.

The coating formulations are applied to appropriate substrates as thin films by a variety of processes illustrative of which are roll coating, dip coating, spray coating, brushing, flexographic, lithographic, and offset web printing processes, and the like. When curing is done by photopolymerization, the film or coating is exposed to light radiation that is rich in ultraviolet light radiation unless special photoinitiators that photolyze in the presence of visible light are used. Particularly useful is radiation of about 200 to about 450 nanometers in wavelength. Illustrative of appropriate light sources are low pressure, medium pressure, and high pressure mercury vapor lamps, xenon and other flash-type lamps, fluorescent lights, lasers, electrodeless mercury lamps, and the like. Other sources of radiant energy such as electron beams, gamma radiation, X-rays, sunlight, and so on can also be used.

Illustrative of such substrates to which the coating compositions can be applied are steel, treated steel, tin plated steel, galvanized steel, treated and untreated aluminum, glass, wood, paper, coated or printed paper, epoxy fiberglass composites, flame retarded epoxy fiberglass composites such as those used in the manufacture of printed circuit boards, graphite fiber reinforced laminates/composites, polymers such as poly(ethylene terephthalate), poly(butylene terephthalate), treated polyethylene and polypropylene, vinyl film, vacuum or vapor deposited aluminum, gold, copper, silver, zinc, nickel, tin, and other metals, electroless nickel, copper-nickel alloys and the like, electrodeposited metals such as silver, copper, nickel, chromium, silver-copper alloys, and the like, glass-reinforced unsaturated-polyester/styrene products, and the like.

Usually proper selection of the above formulation ingredients will yield systems that are easily applied. However, in certain cases it may be desirable to reduce the viscosity by adding one or more inert or nonreactive solvents to the systems in amounts of about one to about 25 weight percent for the purpose of improving flow characteristics or for altering other response characteristics. In certain cases, it may be desirable to use more than 25 percent by weight of the solvent. Illustrative of such solvents are 1,1,1-trichloroethane, ethoxyethanol, ethoxyethyl acetate, ethoxybutanol, ethoxybutanol acetate, butyl acetate, methyl isobutyl ketone, methyl ethyl ketone, propylene glycol methyl, propyl, and butyl ethers, dipropylene glycol alkyl ethers, and the like. It may also be desirable to thicken certain formulations such as those used for screen printing or other end use requiring special rheological responses. Illustrative of the various inert thickening agents that may be employed are fumed silicas, clays, glass spheres or other microballoons, aluminum trihydrate, polymers such as cellulose acetate butyrate, vinyl polymers, phenoxy, acrylates, and the like. The amount of such materials used in a system is dependent on the desired viscosity, thixotropy, or other flow characteristic and is known by those skilled in the art of formulating coatings, inks, and the like.

For purposes of this invention, the term "(meth)acrylate" is contemplated to include acrylates, methacrylates and mixtures thereof, and "(meth)acrylic acid" is contemplated to include acrylic acid, methacrylic acid and mixtures thereof. Also, as used herein, the term "polyol" is contemplated to include all permissible hydrocarbon compounds having 2 or more hydroxyl groups, e.g., diols, triols and the like.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxayalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

GLOSSARY OF TERMS

Insulation Electrical Resistance—This electrical property is a measure of the electrical resistance property or resistance offered by the material to passage of an electrical current. The measurements were made in accordance with method 302, test condition B, of Military Standard 202. Insulating materials are very poor conductors of electricity and offer high resistance and thus the higher the value, the better the insulating property of a material. When temperature increases, insulating resistance decreases. When moisture content of a coating as might be encountered under high humidity conditions increases, insulation resistance decreases. Coatings with a high insulation resistance and the ability to maintain such resistance under high humidity conditions are useful protectors of electrical circuitry.

Double Rubs—Solvent resistance was measured as the number of solvent (methyl ethyl ketone or acetone)

double rubs that were required to cut through the coating. If 100 rubs or more did not cut through the coating, the coating was recorded as >100. To perform the test, the solvent-soaked cloth was rubbed back and forth with hand pressure. A rub back and forth was designated as one "double rub."

Pencil Hardness—Procedure conducted in accordance with ASTM D 3363-74.

Crosshatch Adhesion—Procedure conducted in accordance with ASTM D 3359-87.

Caprolactone Acrylate I—A monoacrylate, hydroxyl-terminated adduct of hydroxyethyl acrylate product commercially available from Union Carbide Chemicals and Plastics Company Inc. as TONE®-M100.

Conformal Coating I—An ultraviolet light curable coating commercially available from Three Bond of America, Inc. under the designation 30A-040. The Material Safety Data Sheet for this product indicates it is 90-95 weight percent acrylic ester, 0-1 weight percent acrylic acid, and 1-10 weight percent polymerization catalyst.

Photoinitiator I—A free radical-generating photoinitiator commercially available from Ciba-Geigy as IRGACURE® 184.

Resin I—Resin used as one package of a two-package coating system and sold as Loctite 361 Resin by Loctite Corp. MSDS indicates composition is 55-60 weight percent 1,1,1-trichloroethane, 20-25 weight percent polyisocyanate prepolymer, 15-20 weight percent 2-ethoxyethyl acetate, 5-7 weight percent methylene bisphenylisocyanate, 0.1-1 weight percent tert-butyl alcohol, and 0.1-1 weight percent methylal. It was recommended that one part of this resin be used with two parts of Activator I.

Activator I—Activator used as one package of a two-package coating system and sold as Loctite 361 Activator by Loctite Corp. MSDS indicates composition is 50-55 weight percent high boiling methacrylate, 25-30 weight percent polyurethane methacrylate resin, 5-7 weight percent acrylic acid, 3-5 weight percent hydoxyalkyl methacrylate, 3-5 weight percent photoinitiator (CAS #947-19-3), and 1-3 weight percent substituted silane. It was recommended that two parts of this activator be used with one part of Resin I.

EXAMPLE 1

Isophorone diisocyanate, 75 grams (0.345 moles), and 100 grams of toluene were charged to a 500 milliliter, 4-neck flask equipped with a mechanical stirrer, nitrogen sparger, inlet and outlet nitrogen connection which also functioned as a feeding port, and thermometer. While sparging with nitrogen and stirring, these ingredients were heated to 80° C. and held at this temperature to remove water. The temperature was then decreased to 55° C. and 30 grams (0.170 moles) of 2-ethyl-3-propyl-1,5-pentanediol were slowly added to the reaction mass. The reaction was allowed to proceed at 55° C. for three hours, and then the reaction mass was allowed to cool to room temperature and stand overnight under a nitrogen blanket. A 20 gram portion of the reaction mass was removed and stored for another purpose. The remainder of the reaction mass was heated to 55° C. while stirring and sparging with air, 35 grams of hydroxyethyl acrylate were slowly added over a 20 minute time period. The reaction was continued at 55° C. for 1.5 hours after which time 0.0284 grams of hydroquinone were added and the reaction was allowed to proceed at 55° C. for an addition three hours. The acrylate-terminated product was then cooled to room temperature and stored in an amber bottle for future use.

EXAMPLES 2 TO 5

Ultraviolet light curable coatings were prepared by placing the ingredients listed in Table A below in amber glass bottles mixing them well. The mixtures were then coated onto a phosphatized steel panels with a No. 20 wire-wound rod and exposed to a 300 watt-per-inch medium pressure mercury vapor light source by placing them on a conveyor operating at 30 feet-per-minute that ran under the ultraviolet light source. In the case of Example 2, two steel panels were coated with the formulation and exposed to ultraviolet light. After exposure one panel was given a post cure or annealing step by placing it in an oven set at 60° C. and the other was not given this post cure. All cured coatings were 1.0 mil in thickness. The coatings were tested by the indicated tests in Table A and the results are given in Table A. As indicated in the footnote to Table A, both the post cured and the nonpost cured coatings of Example 2 had the same properties. The systems of Examples 3, 4, and 5 were also coated onto epoxy/fiberglass substrate, that had a solder Y-test pattern printed on it as described in paragraph 4.7.1.1 of Military Specification I-46058C by a dipping process and cured in the same manner and with the same ultraviolet light source described above. Measurments of electrical insulation resistance for the cured coatings on the Y-test pattern panels were made at various periods after ultraviolet light exposure during which time period the coated panels were kept under summertime, high humidity laboratory conditions and the measurements are given in Table A.

TABLE A

| Ingredients, grams | Examples | | | |
|---|---|---|---|---|
| | 2 | 3 | 4 | 5 |
| Example 1 Acrylate-terminated Product | 10.0 | 8.0 | 6.0 | 4.0 |
| Trimethylolpropane Triacrylate | — | 2.0 | 2.0 | 4.0 |
| Caprolactone Acrylate I | — | — | 1.0 | 2.0 |
| 2,2'-Diethoxyacetophenone | 0.4 | 0.4 | 0.4 | 0.4 |
| Properties of Ultraviolet Light Cured Coatings on Steel Panels | | | | |
| Acetone Double Rubs | 100(1)* | 18(4) | 25(3) | 100(1) |
| Pencil hardness | 2H* | 2H* | 2H | 2H |
| Crosshatch Adhesion, % | 100* | 100 | 100 | 20 |
| Electrical Insulation Resistance of Ultraviolet Cured Coatings of Epoxy-Light Fiberglass Test Patterns, ohms × 10$^{-12}$ | | | | |
| 1 Day after UV exposure | — | >100 | 16 | 14 |
| 5 Days after UV exposure | — | >100 | 7.5 | 8 |

*Same results obtained on coating held at room temperature and post cured at 60° C. for 20 minutes.

The results indicate that the Example 1 polyurethane acrylate can be cured with ultraviolet light when compounded with a free radical generating-photoinitiator such as 2,2'-diethoxyacetophenone alone or in combination with other acrylates to form useful coatings. The measurements of electrical insulation resistance properties indicate that the polyurethane acrylate of Example 1 improves the moisture resistance properties of coatings on printed circuit boards and is useful in conformal coating compositions. In these three examples, the insulation resistance was sufficiently high that the coatings surpassed the requirement of $2.5 \times 10^{12}$ ohms specified in Paragraph 3.9 of Military Specification I-46058C.

EXAMPLE 6 AND CONTROL EXAMPLE A

Conformal Coating I alone (Control A) and modified with the Example 1 polyurethane acrylate (Example 6) were coated onto phosphatized steel and a test pattern board as described in Examples 3-5 and cured in the same manner and with the same ultraviolet light source described in Examples 3-5. Physical properties on the steel panels were determined 6 days after ultraviolet light exposure and electrical resistance measurements were determined at various time intervals indicated in Table B below. Test results are given in Table B.

TABLE B

| Ingredients, grams | Control A | Example 6 |
|---|---|---|
| Conformal Coating I | 10.0 | 8.5 |
| Example 1 Polyurethane Acrylate | — | 1.5 |
| Properties of Ultraviolet Light Cured Coatings on Steel Panels | | |
| Double Acetone Rubs | 60 (3) | 45 (3) |
| Pencil Hardness | 2B | B |
| Crosshatch Adhesion, % | 100 | 100 |
| Electrical Insulation Resistance of Ultraviolet Light Cured Coatings on Epoxy-Fibergalss Test Patterns, ohms $\times 10^{-12}$ | | |
| 1 Day after UV exposure | 0.23 | 0.32 |
| 5 Days after UV exposure | 0.40 | 1.2 |

The results indicate that the polyurethane acrylates of this invention can be used as additives to commercial products without having a deleterious effect on physical characteristics and having an improvement in insulation resistance.

EXAMPLE 7

An 80/20 mixture of 2,4-/2,6-toluene diisocyanate, 60 grams (0.343 moles), and 100 grams of toluene were charged to a 500 milliliter, 4-neck flask equipped with a mechanical stirrer, nitrogen sparger, inlet and outlet nitrogen connection which also functioned as a feeding port, and thermometer. While sparging with nitrogen and stirring, these ingredients were heated to 80° C. and held at this temperature to remove water. The temperature was then decreased to 55° C. and 30 grams (0.170 moles) of 2-ethyl-3-propyl-1,5-pentanediol were slowly added to the reaction mass. The reaction was allowed to proceed at 55° C. for three hours, and then the reaction mass was allowed to cool to room temperature and stand overnight in the reactor with an air sparge. A 20 gram portion of the reaction mass was removed and stored for another purpose.

The remainder of the reaction mass was heated to 55° C. while stirring and sparging with air. When 55° C. was reached, 0.568 grams of 4-methoxyphenol was added followed by addition of 35 grams of hydroxyethyl acrylate over a 45 minute time period. The reaction was continued at 55° C. for three hours after which time the acrylate-terminated product was cooled to room temperature and stored in an amber colored glass container for future use.

EXAMPLES 8-10

Ultraviolet light cured coatings were prepared by blending the ingredients listed in Table C below in a glass container. The mixtures were then coated onto phosphatized steel panels with a No. 20 wire-wound rod and cured in the same manner and with the same ultraviolet light source as described in Examples 2-5. The cured coatings were tested by the indicated tests in Table C and the results are given in Table C.

TABLE C

| | Examples | | |
|---|---|---|---|
| Ingredients, grams | 8 | 9 | 10 |
| Example 7 Polyurethane Acrylate | 9.6 | 4.2 | 2.1 |
| Trimethylolpropane triacrylate | — | 5.4 | 7.5 |
| Photoinitiator I | 0.4 | 0.4 | 0.4 |
| Properties of Ultraviolet Light Cured Coatings on Steel Panels | | | |
| Double Acetone Rubs | 100(1) | 100(1) | 100(1) |
| Pencil Hardness | F | 3H | 3H |

EXAMPLES 11-16 AND CONTROL EXAMPLE B

Ultraviolet light cured coatings were prepared by blending the ingredients listed in Table D below in a glass container. The mixtures were then coated onto phosphatized steel panels with a No. 20 wire-wound rod and cured in the same manner and with the same ultraviolet light source as described in Examples 2-5. The cured coatings were tested by the indicated tests in Table D and the results are given in Table D.

TABLE D

| | Examples | | | | | | |
|---|---|---|---|---|---|---|---|
| Ingredients, grams | B | 11 | 12 | 13 | 14 | 15 | 16 |
| Example 1 Polyurethane Acrylate | — | 3.0 | 7.5 | 11.25 | — | — | — |
| Example 7 Polyurethane Acrylate | — | — | — | — | 3.0 | 7.5 | 11.25 |
| Activator I | 10.0 | 10.0 | 10.0 | 10.0 | 10.0 | 10.0 | 10.0 |
| Resin I | 5.0 | 5.0 | 5.0 | 5.0 | 5.0 | 5.0 | 5.0 |
| Properties of Ultraviolet Light Cured Coatings on Steel Panels | | | | | | | |
| Double Acetone Rubs | 20(3) | 16(3) | 38(3) | 38(3) | 60(3) | 42(3) | 20(3) |
| Pencil Hardness | 3B | B | F | F | 2H | 2H | B |
| Crosshatch Adhesion, % | 100 | 100 | 100 | 100 | 100 | 100 | 100 |

The results indicate that the polyurethane acrylates of this invention can be used with commercial acrylate systems that are used as coatings for the electrical/electronics industry and that by adding them to the commercial systems, solvent resistance and hardness can be varied. The hydrocarbon nature of the polyurethane acrylates of this invention and other results suggest that systems containing them will have improved moisture resistance.

Although the invention has been illustrated by certain of the preceding examples, it is not to be construed as being limited thereby; but rather the invention encompasses the generic area as hereinbefore disclosed. Various modifications and embodiments can be made without departing from the spirit and scope thereof.

We claim:

1. A polyurethane (meth)acrylate comprising the reaction product of (i) a liquid hydrocarbon diol comprised of primary hydroxyl groups and 8 or more carbon atoms in which the primary hydroxy groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less, and/or a derivative of said liquid hydrocarbon diol, (ii) a polyfunctional isocyanate, and (iii) a hydroxyalkyl (meth)acrylate.

2. The polyurethane (meth)acrylate of claim 1 further comprising a polyol different from said liquid hydrocarbon diol or derivative thereof.

3. The polyurethane (meth)acrylate of claim 1 wherein the liquid hydrocarbon diol is represented by the formula:

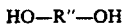

HO—R″—OH wherein R″ is a substituted hydrocarbon residue having 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms.

4. The polyurethane (meth)acrylate of claim 1 wherein the liquid hydrocarbon diol is represented by the formula:

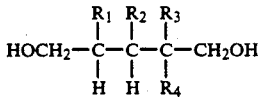

wherein $R_1$ is hydrogen or linear or branched alkyl having 1 to 3 carbon atoms, and $R_2$, $R_3$, and $R_4$ are the same or different and are hydrogen or linear or branched alkyl having 1 to 4 carbon atoms.

5. The polyurethane (meth)acrylate of claim 4 wherein the liquid hydrocarbon diol is represented by the formula:

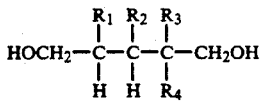

wherein $R_1$ is hydrogen or linear or branched alkyl having from 1 to 3 carbon atoms, and $R_2$, $R_3$ and R are the same or different and are hydrogen or linear or branched alkyl having from 1 to 4 carbon atoms; provided (a) at least 2 of $R_1$, $R_2$, $R_3$ and $R_4$ are other than hydrogen; (b) the total number of carbon atoms in $R_1$, $R_2$, $R_3$ and $R_4$ together is 5 or more except as follows: (i) when $R_2$ is ethyl and one of $R_1$, $R_3$ and $R_4$ is methyl, then the remaining 2 of $R_1$, $R_3$ and $R_4$ can be hydrogen; (ii) when $R_3$ and $R_4$ are independently methyl and propyl, then $R_1$ and $R_2$ can be hydrogen; and (iii) when $R_1$ is methyl and $R_2$ is ethyl and one of $R_3$ and $R_4$ is methyl, then the remaining $R_3$ or $R_4$ can be hydrogen; (c) when the total number of carbon atoms in $R_1$ and $R_2$ is 4 or more, then the total number of carbon atoms in $R_2$ is 3 or less except when $R_1$ is propyl and $R_3$ and $R_4$ are hydrogen, then $R_2$ can be butyl; and (d) when $R_1$ is ethyl and $R_2$ is propyl, then $R_3$ is other than ethyl.

6. The polyurethane (meth)acrylate of claim 4 wherein $R_1$, $R_2$ and $R_3$ are alkyl and $R_4$ is hydrogen.

7. The polyurethane (meth)acrylate of claim 4 wherein $R_1$, $R_2$, $R_3$ and $R_4$ are alkyl.

8. The polyurethane (meth)acrylate of claim 4 wherein $R_1$ and $R_2$ are alkyl and $R_3$ and $R_4$ are hydrogen.

9. The polyurethane (meth)acrylate of claim 4 wherein $R_1$ and $R_2$ are hydrogen and $R_3$ and $R_4$ are alkyl.

10. The polyurethane (meth)acrylate of claim 4 wherein $R_1$ is ethyl, $R_2$ is propyl and $R_3$ and $R_4$ are hydrogen.

11. The polyurethane (meth)acrylate of claim 1 in which the liquid hydrocarbon diol is selected from 3-ethyl-2-methyl-1,5-penlanediol, 2-ethyl-3-propyl-1,5-pentanediol, 2,4-dimethyl-3-ethyl-1,5-pentanediol, 2-ethyl-4-methyl-3-propyl-1,5-pentanediol, 2,3-diethyl-4-methyl-1,5-pentanediol, 3-ethyl-2,2,4-trimethyl-1,5-pentanediol, 2,2-dimethyl-4-ethyl-3-propyl-1,5-pentanediol, 2-methyl-2-propyl-1,5-pentanediol, 2,4-dimethyl-3-ethyl-2-propyl-1,5-pentanediol, 2,3-dipropyl-4-ethyl-2-methyl-1,5-pentanediol, 2-butyl-2-ethyl-1,5-pentanediol, 2-butyl-2,3-diethyl-4-methyl-1,5-pentanediol, 2-butyl-2,4-diethyl-3-propyl-1,5-pentanediol, 3-butyl-2-propyl-1,5-pentanediol, and mixtures thereof.

12. The polyurethane (meth)acrylate of claim 1 in which the liquid hydrocarbon diol is 2-ethyl-3-propyl-1,5-pentanediol.

13. The polyurethane (meth)acrylate of claim 1 wherein the derivative of said liquid hydrocarbon diol is selected from polyesters, silicone-containing compounds, polyols initiated with said liquid hydrocarbon diols, and mixtures thereof.

14. The polyurethane (meth)acrylate of claim 1 in which the polyfunctional isocyanate is represented by the formula:

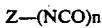

Z—(NCO)n wherein Z is a substituted or unsubstituted hydrocarbon residue and n is a value of from 2 to about 6.

15. The polyurethane (meth)acrylate of claim 1 in which the polyfunctional isocyanate is selected from 2,4-toluene diisocyanate, 2,6-toluene diisocyanate, 4,4'-diphenylmethane diisocyanate (MDI), 4,4'-dicyclohexyldiisocyanate, meta- and para-tetramethyl xylene diisocyanate, 3-isocyanatomethyl-3,5,5-trimethylcyclohexylisocyanate, hexamethylene diisocyanate, 2,2,4- and 2,4,4-trimethylenehexamethylene diisocyanate, meta- and para-phenylene diisocyanate, isophorone diisocyanate, 2,4-, 2,6- and 2,4-/2,6-bromotoluene diisocyanate, 4-bromo-meta-phenylene diisocyanate, ortho- and meta-trifluoromethylphenylisocyanate; ortho, meta-, and para-fluorophenylisocyanate; 4,6-dibromo-meta-phenylene diisocyanate; ortho-, meta-, and para-chlorophenyl isocyanate, 4,4',4''-triisocyanatotriphenylmethane, and mixtures thereof.

16. The polyurethane (meth)acrylate of claim 1 in which the hydroxyalkyl (meth)acrylate is selected from hydroxyethyl acrylate, hydroxyethyl methacrylate, hydroxypropyl acrylate, hydroxypropyl methacrylate, and mixtures thereof.

17. The polyurethane (meth)acrylate of claim 2 wherein said polyol is selected from a poly(tetramethylene oxide) polyol, a polylactone polyol, a polycarbonate polyol, a poly(alkylene oxide) polyol, a polyester polyol, a polyether polyol, and mixtures thereof.

18. The polyurethane (meth)acrylate of claim 1 represented by the formula:

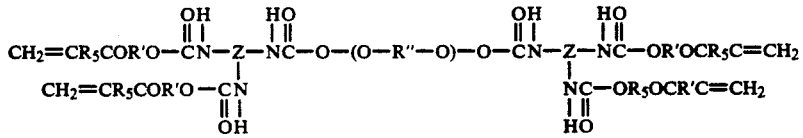

wherein $R_5$ is the same or different and is hydrogen or methyl, R' is the same or different and is a linear or branched alkyl group of about 2 to 6 carbon atoms, R" is a substituted hydrocarbon residue having 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, and Z is the same or different and is a substituted or unsubstituted hydrocarbon residue.

19. A process for preparing a polyurethane (meth)acrylate which comprises (i) contacting a liquid hydrocarbon diol comprised of primary hydroxyl groups and 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less, and/or a derivative of said liquid hydrocarbon diol, with a polyfunctional isocyanate to form an isocyanate-capped prepolymer, and (ii) contacting said isocyanate-capped prepolymer with a hydroxyalkyl (meth)acrylate to form said polyurethane (meth)acrylate.

20. A process for preparing a polyurethane (meth)acrylate which comprises contacting a liquid hydrocarbon diol comprised of primary hydroxyl groups and 8 or more carbon atoms in which the primary hydroxyl groups are separated by 4 or more carbon atoms linearly arranged and in which at least one of said carbon atoms linearly arranged is a disubstituted carbon atom or at least 2 of said carbon atoms linearly arranged are monosubstituted carbon atoms, said liquid hydrocarbon diol existing as a liquid at a temperature of 35° C. or less, and/or a derivative of said liquid hydrocarbon diol, with a polyfunctional isocyanate and a hydroxylalkyl (meth)acrylate to form said polyurethane (meth)acrylate.

21. A curable coating composition comprising the polyurethane (meth)acrylate of claim 1.

22. A cured film prepared from the coating composition of claim 21.

23. The curable coating composition of claim 22 which is cured with thermal or actinic energy or a mixture thereof.

24. An adhesive composition comprising the polyurethane (meth)acrylate of claim 1.

25. An ink composition comprising the polyurethane (meth)acrylate of claim 1.

26. A sealant composition comprising the polyurethane (meth)acrylate of claim 1.

* * * * *